United States Patent [19]
Ferlazzo et al.

[11] 3,997,600
[45] * Dec. 14, 1976

[54] METHOD OF PREPARING ACRYLIC ACID

[75] Inventors: Natale Ferlazzo, Segrate (Milan); Gian Fausto Buzzi, Arona (Novara); Marcello Ghirga, Bresso (Milan), all of Italy

[73] Assignee: Societa' Italiana Resine S.I.R. S.p.A., Milan, Italy

[ * ] Notice: The portion of the term of this patent subsequent to May 11, 1993, has been disclaimed.

[22] Filed: Nov. 18, 1974

[21] Appl. No.: 524,834

[30] Foreign Application Priority Data

Nov. 28, 1973 Italy .................................. 31750/73

[52] U.S. Cl. ....................... 260/530 N; 260/486 R; 260/533 N
[51] Int. Cl.² ......................................... C07C 51/32
[58] Field of Search ........ 260/530 N, 533 N, 604 R

[56] References Cited
UNITED STATES PATENTS 3,819,685   6/1974   Grasselli ....................... 260/530 N

*Primary Examiner*—Vivian Garner
*Attorney, Agent, or Firm*—Sughrue, Rothwell, Mion, Zinn & Macpeak

[57] ABSTRACT

Acrylic acid is prepared by contacting an oxidation catalyst with a gaseous mixture containing acrolein, oxygen and methanol. A proportion by volume from 0.05 to 0.5% methanol and a molar ratio of acrolein to methanol from 10:1 to 100:1 are maintained in the said mixture the catalyst is defined by one of the general formulae:

$Mo_a V_b Me_c O_x$
$Mo_a W_d Me_c O_y$
$Mo_a V_b W_d Me_c O_z$ wherein Me is Cr, Mn, Fe, Co, Ni, Cu, Zn, Ag, Cd, Au, Hg, Na, Ba, Ca, Ce, Bi, Th, U, Pb, Sn, Sb, P or B; and wherein a is a value from 6 to 12, b from 1 to 6, c from 0 to 5, d from 1 to 6, x from 20.5 to 58.5, y from 21 to 61.5 and z from 23.5 to 76.5. The reaction is carried out at a temperature not exceeding 320° C.

14 Claims, No Drawings

METHOD OF PREPARING ACRYLIC ACID

The invention relates to an improved method of preparing acrylic acid by catalytic oxidation of acrolein.

U.S. Pat. application Ser. No. 420,344 filed 29th Nov., 1973, now U.S. Pat. No. 3,956,376, describes a process for preparing acrolein from propylene, or of acrylic acid starting from propylene, acrolein or mixtures of both, by contacting said reactants and oxygen with an oxidation catalyst at a temperature of 320° C at least, in the presence of small quantities of methanol.

According to the above-mentioned application the use of methanol under operational conditions results in an increased conversion and selectivity in useful oxidation products.

The present invention provides substantially improvements in the method of oxidation of acrolein to acrylic acid, by contacting at a temperature not exceeding 320° C a gaseous stream containing acrolein and oxygen with a catalyst belonging to a particular class and in the presence of small quantities of methanol.

The catalysts employed in the process of the invention belong to the class of oxyesterification catalysts used for catalysing the reaction between unsaturated aldehydes (acrolein or methacrolein), oxygen and a lower aliphatic alcohol (methanol and ethanol) in the formation of the corresponding acrylic esters.

Thus, the invention provides a process for preparing acrylic acid by contacting a gaseous mixture containing acrolein and oxygen with an oxidation catalyst characterised in that:

the oxidation catalyst belongs to those defined by the general formulae:

1. $Mo_a\ V_b\ Me_c\ O_x$ .
2. $Mo_a\ W_d\ Me_c\ O_y$
3. $Mo_a\ V_b\ W_d\ Me_c\ O_z$ wherein Me stands for chromium, manganese, iron, cobalt, nickel, copper, zinc, silver, cadmium, gold, mercury, sodium, barium, calcium, cerium, bismuth, thorium, uranium, lead, antimony, tin, phosphorus and boron; a ranges from 6 to 12; b from 1 to 6; c from 0 to 5; d from 1 to 6; x from 20.5 to 58.5; y from 21 to 61.5; z from 23.5 to 76.5;

the gaseous mixture contains a proportion of methanol from 0.05 to 0.5% by volume, a molar ratio of acrolein to methanol of from 10:1 to 100:1 being maintained in said mixture, the contacting reaction is carried out at a temperature not exceeding 320° C.

The catalysts can be prepared by a process comprising the steps of dissolving in water compounds of the metals present in the catalyst, precipitating the said compounds by evaporating the solution and heat-treating the precipitated solids at high temperature (130° to 600° C) during a period of not less than 2 hours.

The catalyst can additionally comprise a support in a proportion up to 90 parts by weight to 100 parts by weight of the finished catalyst. Useful supports are: silica, alumina, and oxides of zirconium, titanium and magnesium, silica being the preferred support.

According to the process of the present invention, the catalyst, in the form of a stationary, fluidized or movable bed, is contacted with a gaseous mixture containing acrolein, oxygen and small quantities of methanol.

More particularly, in the gaseous mixture a concentration by volume of 1 to 8% acrolein, 0.5 to 20% oxygen, 0.05 to 0.5% methanol is conveniently maintained.

The remaining part of the gaseous mixture generally consists substantially of inert gases such as nitrogen, carbon dioxide and steam. It was found that the use of steam as diluent in the gaseous mixture is generally advantageous. The molar ratio of acrolein to molecular oxygen in the gaseous mixture is conveniently in the range from 0.1:1 to 4:1, preferably from 0.2:1 to 2:1. The molar ratio of acrolein to methanol is from 10:1 to 100:1.

The proportion of methanol should conveniently not exceed the maximum limit otherwise methyl ester of acrylic acid is formed. On the other hand, the methanol proportion should be below the lower limit, otherwise the advantages of the invention are not obtained.

Acrolein can be supplied as such; however, the gases obtained in the catalytic oxidation of propylene, and containing acrolein in addition to unreacted propylene, oxygen and inert gases are suitable for the purposes of the present invention.

These gases can be directly used in the process of the invention after admixture with methanol, possibly oxygen, in such a proportion as to bring the composition of the resulting gaseous mixture within the previously defined ranges.

Oxygen can be supplied as such or in the form of gases containing molecular oxygen, such as air.

A peculiar feature of the process of the invention is the adoption of a relatively low temperature, not exceeding in any case 320° C. Generally, a temperature from 180° to 320° C is adopted, the best results being obtained with a reaction temperature from 200° to 280° C. The reaction can moreover be carried out at atmospheric pressure or superatmospheric pressure such as up to 5 kg/sq.cm. It is also possible, though not convenient, to operate at a subatmospheric pressure.

Finally, the contact period under reaction conditions is generally from 0.1 to 40 seconds, a period from 1 to 20 seconds being preferred.

By proceeding under the above described conditions, the conversion calculated on acrolein is always above 95% by moles, the selectivity for the acrylic acid calculated with respect to converted acrolein being at least of 95% by moles.

The invention is essentially based on the discovery that the use of very small quantities of methanol in oxidizing acrolein to acrylic acid in the presence of the aforesaid catalyst increases the conversion and selectivity to extraordinarily high values without any appreciable formation of methyl acrylate. This peculiar effect derives from the use of methanol, since other aliphatic alcohols such as ethanol do not afford similar effects.

The following experimental examples further illustrate the invention without, however, imposing any limitation thereon.

EXAMPLE 1

13.3 g ammonium paramolybdate $(NH_4)_6Mo_7O_{24}.4H_2O$, 3.2 g tungstic acid $H_2WO_4$ and 1.5 g ammonium metavanadate $NH_4VO_3$ are dissolved at 80° C in 400 ml of a 16% by weight aqueous ammonia solution, followed by slow evaporation at 95° C to dryness and treatment in an oven during 2.5 hours at 120° C and during 2 hours at 300° C.

The resulting solids are finely ground to a powder 50 to 100 microns in grain size.

8.9 g ferrous oxalate Fe(COO)$_2$ 2 H$_2$O are then dissolved in 120 ml aqueous nitric acid with an acid concentration of 65% by weight, containing 5 ml hydrogen peroxide at 120 volumes concentration (1 vol. liquid develops 120 volumes gaseous O$_2$). The resulting solution is slowly evaporated to dryness. The solid residue is admixed with 100 ml water, and the powder obtained as described above from the compounds of molybdenum, vanadium and tungsten is dispersed therein while vigorously stirring. While further stirring, slow evaporation at 95° C to dryness is effected, whereupon the temperature is allowed to rise up to 180° C. The resulting solids are finely ground, dispersed in 100 ml water then brought to dryness. The latter steps are carried out three times under the above described conditions.

The solids are finally heat-treated by slowly raising the temperature during three hours to 380° C, this temperature being then further maintained during three hours in a nitrogen atmosphere.

EXAMPLE 2

6 ml catalyst prepared as described in example 1, are ground, sieved to 50 to 150 microns grain size and charged to an AISI 316 steel vertical tubular reactor, 8 mm in bore diameter.

A gaseous mixture is fed at the reactor top, with the following composition by volume: acrolein 4.1%, steam 35.0%, air 30.0%, methanol 0.1%, the remaining percentage being nitrogen.

The reaction is carried out at a temperature of 245° C with the catalyst in the form of a stationary bed, at atmospheric pressure and with a contact period measured under reaction conditions of 4.0 seconds.

This leads to a conversion of 96% with respect to acrolein, the selectivity for acrylic acid with respect to the reacted acrolein being 95 mol %.

EXAMPLE 3 (COMPARATIVE EXAMPLE)

The procedure is exactly as described in Example 2 with the only difference that no methanol is contained in the gaseous feed to the reactor.

A conversion of 95% with respect to acrolein and a selectivity for acrylic acid with respect to the reacted acrolein of 91 mol % are obtained.

EXAMPLE 4

6.92 g cobalt acetate Co(CH$_3$COO)$_2$. 4H$_2$O are dissolved in 75 ml water.

1.1 g ammonium metavanadate, 8.9 g ammonium paramolybdate and 2.2 g tungstic acid are separately dissolved at 80° C in a 250 ml beaker in 200 ml of a 16% by weight ammonia aqueous solution. The solution is brought to boiling temperature, water is slowly evaporated and the solid residue is dried in an oven during 2 hours at 120° C.

The dry residue is admixed with the cobalt acetate solution, the resulting mixture being heated to its boiling point and slowly evaporated, followed by thorough drying and rise in temperature to 170° C. This temperature is maintained during 20 minutes. The mass is cooled, taken up with 100 ml water, heated to boiling temperature and thoroughly dried. The temperature is then raised to 200° C and maintained as such during 30 minutes. The resulting solids are admixed with 50 ml water, brought to boiling temperature and dried, whereupon the temperature is raised to 200° C and maintained as such during 30 minutes, whereupon treatment with a nitrogen stream during 2 hours at 280° C and further two hours at 380° C is effected.

EXAMPLE 5

6 ml catalyst prepared as described in Example 4, ground and sieved for obtaining a fraction of 100 to 150 microns grain size, are charged to an AISI 316 steel reactor 8 mm in bore diameter. A gaseous mixture is fed at the reactor top, with the following composition by volume: acrolein 2.5%, methanol 0.05%, air 18%, steam 25%, the remainder being nitrogen. The reaction is carried out with the catalyst in the form of stationary bed, at a temperature of 228° C and atmospheric pressure, with a contact period of 4.5 sec. measured under reaction conditions, whereby acrolein conversion of 100% is obtained. The selectivity for acrylic acid with respect to the converted acrolein amounts to 95 mol %.

EXAMPLE 6 (COMPARATIVE EXAMPLE)

The procedure described in Example 5 is followed with the difference that no methanol is contained in the gaseous feed to the reactor. The conversion with respect to acrolein amounts to 98%, the selectivity for acrylic acid with respect to the reacted acrolein being of 89 mol %.

EXAMPLE 7

6.62 g ammonium paramolybdate, 2.24 g tungsten salt (NH$_4$)$_{10}$W$_{12}$O$_{41}$.5H$_2$O and 2.51 g ammonium metavanadate are dissolved in 200 ml 16% by weight ammoniacal aqueous solution at 80° C while stirring, followed by slow evaporation to dryness at 90°–100° C and treatment of the solids in an oven at 120° C during two hours, whereupon the solids are finely ground and suspended in 50 ml water. The suspension is admixed while stirring with 5.76 g copper nitrate dissolved in 50 ml water, then slowly evaporated at 95° C and heated to 200° C, this temperature being maintained during 20 minutes. The solids are taken up with 50 ml water, evaporated to dryness and heated at 200° C, during 30 minutes. The latter steps are then carried out again twice. Finally treatment in a nitrogen atmosphere during two hours at 280° C and two further hours at 380° C is effected.

EXAMPLE 8

An AISI 316 steel reactor, 10 mm in bore diameter is charged with 6 ml of the catalyst prepared as described in example 7, 50 to 150 microns in grain size, to form a stationary bed.

The reactor is fed at the top with a gaseous mixture obtained in the catalytic oxidation of propylene, admixed with methanol to obtain the following composition by volume: acrolein 4.5%, methanol 0.1%, propylene 0.2%, oxygen 10.3%, CO and CO$_2$ 1.5%, steam 18.7%, the remaining percentage being nitrogen.

The reaction is carried out at 248° C and atmospheric pressure, with a contact period under reaction conditions of 3 seconds.

Under these conditions acrolein is converted by 98.5% with a selectivity for acrylic acid with respect to the reacted acrolein of 95.8 mol %.

EXAMPLE 9 (COMPARATIVE EXAMPLE)

The procedure described in Example 8 is followed with the only difference that no methanol is contained in the gaseous feed to the reactor. The conversion with respect to acrolein amounts to 98%, the selectivity for acrylic acid with respect to the reacted acrolein being of 93 mol %.

EXAMPLE 10

8.1 g ammonium paramolybdate, 2.1 g ammonium metavanadate and 1.12 g tungsten salt as described in Example 7 are dissolved in 200 ml aqueous solution containing 16% by weight ammonia, maintained at 80° C till a clear orange-coloured solution is obtained. The latter is heated to its boiling point and admixed with 14 ml of a silica-sol known under the trade name of LUDOX AS containing 30% by weight silica.

The resulting solution is admixed at 95° C with 5.8 g copper nitrate dissolved in 100 ml aqueous solution containing 32% by weight ammonia, slowly evaporated to dryness and the solids are finally treated during three hours at 420° C in a nitrogen stream.

EXAMPLE 11

6 ml of the catalyst described in example 10, 50 to 150 microns in grain size, are charged to an AISI 316 stainless steel reactor 10 mm in bore diameter, to form a stationary bed.

The reactor is fed at the top with a gaseous mixture obtained in the catalytic oxidation process of propylene to acrolein and acrylic acid and having after admixture of methanol the following composition by volume: acrylic acid 0.1%, acrolein 2.3%, propylene 0.2%, methanol 0.05%, steam 17.6%, CO and $CO_2$ 0.9%, oxygen 3.6%, the remainder being nitrogen.

The reaction is carried out at 260° C, at a pressure of 400 mmHg column above atmospheric pressure, and with a contact period of two seconds measured under reaction conditions.

Under these conditions the conversion of acrolein amounts to 99%, the selectivity for acrylic acid with respect to the reacted acrolein amounting to 97 mol. %.

EXAMPLE 12 (COMPARATIVE EXAMPLE)

This test is carried out as described in Example 11, with the only difference that no methanol is contained in the gaseous feed to the reactor.

The resulting conversion of acrolein amounts to 98%, the selectivity for acrylic acid with respect to the converted acrolein being of 86 mol. %

What we claim is:

1. A method of preparing acrylic acid comprising contacting with an oxidation catalyst at a temperature not exceeding 320° C a gaseous mixture comprising acrolein, oxygen and methanol in a proportion by volume from 0.05 to 0.5% of methanol and a molar ratio of acrolein to methanol from 10:1 to 100:1, and wherein the said catalyst is a calcined metal oxide catalyst chosen from the group of compounds defined by the following formulae:

$Mo_a V_b Me_c O_x$
$Mo_a W_d Me_c O_y$
$Mo_a V_b W_c Me_c O_z$ wherein Me is an element chosen from the group consisting of chromium, manganese, iron, cobalt, nickel, copper, zinc, silver, cadmium, gold, mercury, sodium, barium, calcium, cerium, bismuth, thorium, uranium, lead, antimony, tin, phosphorus and boron; and wherein $a, b, c, d, x, y, z$ are numbers varying, respectively: $a$ from 6 to 12, $b$ from 1 to 6, $c$ from 0 to 5, $d$ from 1 to 6, $x$ from 20.5 to 58.5, $y$ from 21 to 61.5 and $z$ from 23.5 to 76.5.

2. The method of claim 1, wherein a molar ratio of acrolein to oxygen from 0.1:1 to 4:1 is maintained in the said gaseous mixture.

3. The method of claim 2, wherein the molar ratio of acrolein to oxygen is from 0.2:1 to 2:1.

4. The method of claim 1, wherein the gaseous mixture comprises the gases obtained in a catalytic oxidation process of propylene to acrolein.

5. The method of claim 4, wherein the gaseous mixture consists essentially of the said gases admixed with methanol.

6. The method of claim 4, wherein the gaseous mixture consists essentially of the said gases admixed with methanol and oxygen.

7. The method of claim 1, wherein the temperature is from 180° to 320° C.

8. The method of claim 1, wherein the temperature is from 200° to 280° C.

9. The method of claim 1, wherein the pressure is from atmospheric pressure up to 5 kg/sq.cm.

10. The method of claim 1, wherein the contact period is from 0.1 to 40 seconds.

11. The method of claim 1, wherein the contact period is from 1 to 20 seconds.

12. The method of claim 1, wherein the gaseous mixture comprises acrolein in a proportion of from 1 to 8 vol % and oxygen in a proportion of from 0.5 to 20 vol %, the remainder consisting substantially of inert gases.

13. The method of claim 12, wherein a molar ratio of acrolein to oxygen from 0.1:1 to 4:1 is maintained in the said gaseous mixture and the latter is contacted with the catalyst at a temperature from 180° to 320° C, a pressure from atmospheric pressure up to 5 Kg/sq.cm. and during a period of from 0.1 to 40 seconds.

14. The method of claim 13, wherein the gaseous mixture comprises the gases obtained in the catalytic oxidation of propylene to acrolein.

\* \* \* \* \*